United States Patent
Ürögdi et al.

(10) Patent No.: US 7,126,002 B2
(45) Date of Patent: Oct. 24, 2006

(54) PYRIDINE-1-OXIDE DERIVATIVE, AND PROCESS FOR ITS TRANSFORMATION INTO PHARMACEUTICALLY EFFECTIVE COMPOUNDS

(75) Inventors: László Ürögdi, Budapest (HU); Zita Jegesné-Csákai, Kunszentmiklós (HU); Lajos Gruber, Budapest (HU); László Ötvös, Budapest (HU); József Tóth, Budapest (HU); István Tömösközi, Budapest (HU); Anió Szakácsné-Schmidt, Veszprém (HU); Ferencné Reider, Veszprém (HU); Mária Schneiderné-Barlay, Veszprém (HU)

(73) Assignee: CytRx Corporation, Los Angeles, CA (US)

( * ) Notice: Subject to any disclaimer, the term of this patent is extended or adjusted under 35 U.S.C. 154(b) by 180 days.

(21) Appl. No.: 10/257,755

(22) PCT Filed: Apr. 17, 2001

(86) PCT No.: PCT/HU01/00046

§ 371 (c)(1),
(2), (4) Date: Jan. 28, 2003

(87) PCT Pub. No.: WO01/79174

PCT Pub. Date: Oct. 25, 2001

(65) Prior Publication Data

US 2004/0006232 A1 Jan. 8, 2004

(30) Foreign Application Priority Data

Apr. 18, 2000 (HU) .............................................. 0001583

(51) Int. Cl.
C07D 401/12 (2006.01)
C07D 211/06 (2006.01)

(52) U.S. Cl. ......................................... 546/193; 514/318
(58) Field of Classification Search ................. 546/193; 514/318

See application file for complete search history.

(56) References Cited

U.S. PATENT DOCUMENTS

| 5,147,879 | A | 9/1992 | Nagy et al. | |
| 5,296,606 | A | 3/1994 | Nagy et al. | |
| 6,649,628 | B1 * | 11/2003 | Kurthy et al. | 514/318 |
| 6,653,326 | B1 * | 11/2003 | Vigh et al. | 514/318 |

FOREIGN PATENT DOCUMENTS

| WO | WO 97/13504 | 4/1997 |
| WO | WO 97/16439 | 5/1997 |
| WO | WO 00/50403 | 8/2000 |

* cited by examiner

Primary Examiner—Celia Chang
(74) Attorney, Agent, or Firm—Fish & Neave IP Group Ropes & Gray LLP

(57) ABSTRACT

The invention relates to N-[2-hydroxy-3-(1-piperidinyl)-propoxy]-pyridine-1-oxide-3-carboxamidine and its optically active enantiomers. (R)-(−)-N-[2-hydroxy-3-(1-piperidinyl)-propoxy]-pyridine-1-oxide-3-carboxamidine and (S)-(+)-N-[2-hydroxy-3-(1-piperidinyl)-propoxy]-pyridine-1-oxide-3-carboxamidine. Furthermore, the invention relates to the preparation of N-[2-hydroxy-3-(1-piperidinyl)-propoxy]-pyridine-1-oxide-3-carboxyimidoyl chloride, which may be used as an active ingredient of medicaments, and the preparation of the optically active enantiomers of this compound using the compounds of the invention as intermediate substances.

5 Claims, 1 Drawing Sheet

PYRIDINE-1-OXIDE DERIVATIVE, AND PROCESS FOR ITS TRANSFORMATION INTO PHARMACEUTICALLY EFFECTIVE COMPOUNDS

TECHNICAL FIELD

The invention relates to a new pyridine-1-oxide-3-carboxamidine derivative, which may be used as intermediate in the production of the active ingredient of pharmaceutical products for the treatment of diabetic complications. Namely, the invention relates to the compound N-[2-hydroxy-3-(1-piperidinyl)-propoxy]-pyridine-1-oxide-3-carboxamidine and its optically active enantiomers, (R)-(−)-N-[2-hydroxy-3-(1-piperidinyl)-propoxy]-pyridine-1-oxide-3-carboxamidine and (S)-(+)-N-[2-hydroxy-3-(1-piperidinyl)-propoxy]-pyridine-1-oxide-3-carboxamidine. Furthermore, the invention relates to the preparation of N-[2-hydroxy-3-(1-piperidinyl)-propoxy]-pyridine-1-oxide-3-carboximidoyl chloride, which may be used as an active ingredient of medicaments, and the preparation of the optically active enantiomers of this compound using the compounds of the invention as intermediate substances.

BACKGROUND ART

N-[2-hydroxy-3-(1-piperidinyl)-propoxy]-pyridine-3-carboximidoyl chloride, along with several related compounds, is known from WO 97/16439 as an effective agent suitable for increasing the chaperone expression of cells. In this publication, the compound is defined as a novel compound, and the N-oxide derivatives of the compound are also claimed, but there is no specific mention of the N-[2-hydroxy-3-(1-piperidinyl)-propoxy]-pyridine-1-oxide-3-carboximidoyl chloride, and its preparation process is not described either.

N-[2-hydroxy-3-(1-piperidinyl)-propoxy]-pyridine-1-oxide-3-carboximidoyl chloride is disclosed and claimed as a novel compound in WO 00/50403, and its production process is described there as well. The compound is produced by the oxidation of the N-[2-hydroxy-3-(1-piperidinyl)-propoxy]-pyridine-3-carboximidoyl chloride. In the course of oxidation with peracids, the bis-N-oxide derivative oxidized on the N-atoms of both the piperidine ring and the pyridine ring, or the piperidine-N-oxide derivative are formed preferentially, and therefore the oxidation with peracid must be performed in the presence of a strong acid to ensure the dominance of the formation of the pyridine-N-oxide derivative in the course of the oxidation process. The yield of this process, however, is not satisfactory. The optically active enantiomers of the N-[2-hydroxy-3-(1-piperidinyl)-propoxy]-pyridine-1-oxide-3-carboximidoyl chloride are also described in WO 00/50403. They are prepared in a way similar to the preparation of the raceme compound using the suitable optically active starting substances.

Considering the fact that the N-[2-hydroxy-3-(1-piperidinyl)-propoxy]-pyridine-1-oxide-3-carboximidoyl chloride and its optically active enantiomers are not only useful in the treatment of diabetic complications, primarily retinopathy, neuropathy and nephropathy, but simultaneously reduce chronic insulin resistance, these compounds are valuable active ingredients in pharmaceutical products. However, in order for these compounds to be useful in the pharmaceutical industry, an easier process is necessary for their production.

DISCLOSURE OF INVENTION

Figure 1:
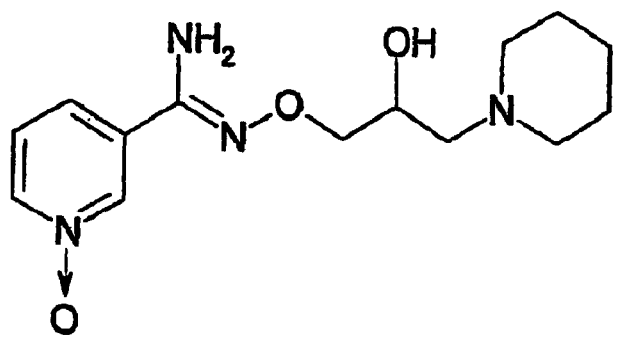
FIG. 1 shows the compound of formula (I): N-[2-hydroxy-3-(1-piperidinyl)-propoxy]-pyridine-1-oxide-3-carboxamidine.

We have found that N-[2-hydroxy-3-(1-piperidinyl)-propoxy]-pyridine-1-oxide-3-carboxamidine of formula (I) (FIG. 1), which is a new compound, is useful as an intermediate for making possible the simple production of N-[2-hydroxy-3-(1-piperidinyl)-propoxyl-pyridine-1-oxide-3-carboximidoyl chloride in high purity and in a high yield.

Based on this observation, the present invention relates to the N-[2-hydroxy-3-(1-piperidinyl)-propoxy]-pyridine-1-oxide-3-carboxamidine, and its acid addition salts. The invention also relates to the optically active enantiomers of the aforementioned compound, the (R)-(−)-N-[2-hydroxy-3-(1-piperidinyl)-propoxy]-pyridine-1-oxide-3-carboxamidine and the (S)-(+)-N-[2-hydroxy-3-(1-piperidinyl)-propoxy]-pyridine-1-oxide-3-carboxamidine, and the acid addition salts of these compounds.

Hereafter, "optically active enantiomer" refers to a compound whose optical purity is at least 80%, preferably at least 90%, most preferably at least 96%, that is, the compound contains at least this mass ratio of the specified optically active enantiomer. "Acid addition salts" refers to salts produced from the compounds with mineral or organic salts, by the known process.

As mentioned above, the compounds of the invention may be used as intermediates in the production of N-[2-hydroxy-3-(1-piperidinyl)-propoxy]-pyridine-1-oxide-3-carboximidoyl chloride. Therefore, the invention relates to the use of N-[2-hydroxy-3-(1-piperidinyl)-propoxy]-pyridine-1-oxide-3-carboxamidine and its optically active enantiomers in the preparation of N-[2-hydroxy-3-(1-piperidinyl)-propoxy]-pyridine-1-oxide-3-carboximidoyl chloride and its optically active enantiomers.

The compound N-[2-hydroxy-3-(1-piperidinyl)-propoxy]-pyridine-1-oxide-3-carbox-amidine of the invention is preferably prepared by the following method.

Figure 2:
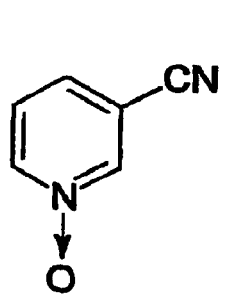
FIG. 2 shows the compound of formula (II): 3-cyano-pyridine-1-oxide.

3-cyano-pyridine is used as a starting compound, and the 3-cyano-pyridine-1-oxide of formula (II) (FIG. 2), which is known from the literature [J. Chem. Soc. 3680 (1959)], can be produced by oxidation. A peracid is used as oxidant, preferably m-chloro-perbenzoic acid. The thus obtained product may be purified by crystallization, but the raw product may also be used in the next step of the synthesis.

Figure 3:
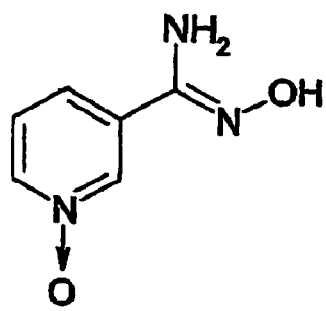
FIG. 3 shows the compound of formula (III): 3-pyridine-amidoxim-1-oxide.

By reacting the 3-cyano-pyridine-1-oxide of formula (II) with hydroxylamine, 3-pyridine-amidoxim-1-oxide of formula (III) (FIG. 3) is produced. The reaction is performed in a suitable aqueous solution, at room temperature, by reacting 3-cyano-pyridine-1-oxide with hydroxylamine, added in excess and liberated in water in situ from its hydrochloride salt with sodium bicarbonate. The product precipitates, therefore it can easily be isolated and purified by crystallization.

Figure 4:
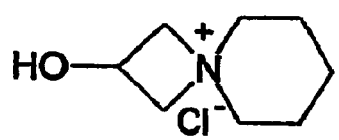
FIG. 4 shows the compound of formula (IV): 2-hydroxy-4-azoniaspiro[3,5]nonane chloride.

N-(2-hydroxy-3-(1-piperidinyl)-propoxy]-pyridine-1-oxide-3-carboxamidine of formula (I) is prepared from the 3-pyridine-amidoxim-1-oxide of formula (III), by reacting the compound with a reactive 3-(1-piperidine)-2-hydroxypropane derivative. As a reagent, a 1-halo- or 1,2-epoxy-derivative may be used, but preferably a cyclic derivative, a halide of 2-hydroxy-4-azoniaspiro[3,5]nonane should be used as reagent. The most preferable reagent is the 2-hydroxy-4-azoniaspiro[3,5]nonane chloride of formula IV (FIG. 4). The reaction is performed in an alkaline medium, using a suitable alcohol, preferably an alkanol of 1–3 carbon atoms, more preferably ethanol as solvent. The reagents may be added in any order. Preferably, the reactive 3-(1-piperidino)-2-hydroxy-propane derivative is applied in slight excess. The reaction is performed at an elevated temperature, preferably at the boiling-point of the solvent.

The thus obtained compound of formula (I) is either isolated as a base and used as intermediate in the preparation of the biologically effective N-[2-hydroxy-3-(1-piperidinyl)-propoxy]-pyridine-1-oxide-3-carboximidoyl chloride, or the compound is transformed into an acid addition salt with a mineral or organic acid. Thus mono- or dihydrochloride, maleate, or any other acid addition salt may be prepared which are suitable for the use of the compound as intermediate in the preparation of the above mentioned end product. However, it is not necessary to isolate the N-[2-hydroxy-3-(1-piperidinyl)-propoxy]-pyridine-1-oxide-3-carboxamidine to be used as intermediate. The next step in the synthesis of N-[2-hydroxy-3-(1-piperidinyl)-propoxy]-pyridine-1-oxide-3-carboximidoyl chloride may be performed without the isolation of the compound of formula (I) as well.

When preparing of an optically active product is desired, the compound of formula (I), prior to the transformation, can be resolved by reacting it with an optically active acid suitable for the formation of a diastereomer salt pair, by the well known methods of resolution. When the salt of the required optical purity is obtained, the optically active base may be liberated from it. Thereafter, if needed, an acid addition salt may be produced from the base with a mineral or organic acid. Either the base or the salt may then be used for the next step of the process of the invention.

Figure 5:
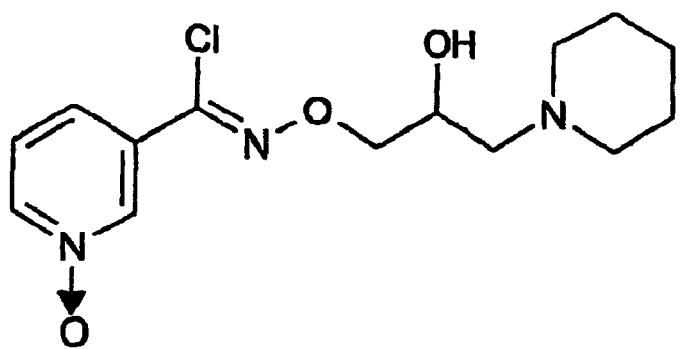
FIG. 5 shows the compound of formula (V): N-[2-hydroxy-3-(1-piperidinyl)-propoxy]-pyridine-1-oxide-3-carboximidoyl chloride.

According to the invention, N-[2-hydroxy-3-(1-piperidinyl)-propoxy]-pyridine-1-oxide-3-carboxamidine of formula (I) is transformed into N-(2-hydroxy-3-(1-piperidinyl)-propoxyl-pyridine-1-oxide-3-carboximidoyl chloride by diazotation in the presence of hydrochloric acid. The diazotation is performed by the usual method, at a temperature of between −5° C. and 0° C., with the slow addition of an alkali-nitrite, preferably sodium-nitrite. In the presence of hydrochloric acid, the thus obtained diazonium salt decomposes at the temperature of the diazotation into N-[2-hydroxy-3-(1-piperidinyl)-propoxy]-pyridine-1-oxide-3-carboximidoyl chloride of formula (V) (FIG. 5). Then the reaction mixture is alkalified, while cooling, and the product is isolated in the form of a base by the usual method. The obtained base may be further purified if needed, or transformed into an acid addition salt with a mineral or organic acid. Preferably, maleate or citrate is formed from the compound of formula (V), but it may also be transformed into hydrochloride, dihydrochloride or any pharmaceutically acceptable acid addition salt.

The required optically active enantiomers of the N-[2-hydroxy-3-(1-piperidinyl)-propoxy]-pyridine-1-oxide-3-carboximidoyl chloride of formula (V) prepared by diazotation are prepared by resolution from the raceme compound. The resolution is again performed by the formation of a diastereomer salt pair, preferably with dibenzoyl-tartaric acid, using its suitable optically active form for the salt formation.

If the above described diazotation of N-[2-hydroxy 3-(1-piperidinyl)-propoxy]-pyridine-1-oxide-3-carboxamidine of formula (I) is performed on an optically active enantiomer, the enantiomer of the N-[2-hydroxy-3-(1-piperidinyl)-propoxy]-pyridine-1-oxide-3-carboximidoyl chloride of formula (V) of opposite rotation is formed, of satisfactory optical purity. Therefore, according to another version of the process of the invention, the optically active N-[2-hydroxy-3-(1-piperidinyl)-propoxy]-pyridine-1-oxide-3-carboximidoyl chloride of formula (V) is prepared by performing the above described diazotation on the suitable optically active enantiomer of N-[2-hydroxy-3-(1-piperidinyl)-propoxy]-pyridine-1-oxide-3-carboxamidine of formula (I). The thus obtained base may be further purified if needed, or an acid addition salt may be formed with a mineral or organic acid.

The advantage of the invention is that, by the use of the compound of formula (I) of the invention as intermediate, it makes possible the production of highly pure N-[2-hydroxy-3-(1-piperidinyl)-propoxy]-pyridine-1-oxide-3-carboximidoyl chloride, which has valuable biological effects. Contrary to the process described in WO 00/50403 mentioned in the introduction, in which this compound is prepared by the oxidation of N-[2-hydroxy-3-(1-piperidinyl)-propoxy]-pyridine-3-carboximidoyl chloride, in this current process the appearance of the products of competitive reactions need not be taken into account. By the process of the invention, the base form of N-[2-hydroxy-3-(1-piperidinyl)-propoxy]-pyridine-1-oxide-3-carboximidoyl chloride is obtained in high purity. Up to this point, this was only possible by lengthy purification, or by liberation of the base from the maleate salt.

A further advantage of the invention is that the N-[2-hydroxy-3-(1-piperidinyl)-propoxy]-pyridine-1-oxide-3-carboxamidine of the invention may be produced by the merge of the steps described above and illustrated in the following examples in greater detail, without the isolation and/or purification of each intermediate product, still obtaining satisfactory purity. This way, the production of the intermediate N-[2-hydroxy-3-(1-piperidinyl)-propoxy]-pyridine-1-oxide-3-carboxamidine becomes possible in the circumstances of pharmaceutical production, which makes possible the industrial production of the biologically effective N-[2-hydroxy-3-(1-piperidinyl)-propoxy]-pyridine-1-oxide-3-carboximidoyl chloride.

BEST MODE OF CARRYING OUT THE INVENTION

The invention is illustrated by the following examples.

EXAMPLE 1

The preparation of 3-cyano-pyridine-1-oxide (compound of formula II)

86 g (0.378 mol) of 76% m-chloro perbenzoic acid is dissolved in 730 ml of dichloro-methane at 20–25° C., and 220 ml of the solution of 38.3 g (0.378 mol) of 3-cyano-pyridine in dichloro-methane is added at 20–28° C. The reaction mixture is stirred at 20–24° C. for 24 hours. At the end of the reaction, the solvent is evaporated. The evaporation residue is digerated in 430 ml of methyl terc-butyl ether, the precipitate is filtered, washed and dried. 59 g of raw product is obtained.

By recrystallizing the raw product twice from hot ethanol, 36.6 g (80%) of pure 3-cyano-pyridine-1-oxide is obtained, which melts at 174–176.5° C. (literature: 174–175° C.; J. Chem. Soc. 3680 (1959)).

EXAMPLE 2

The preparation of 3-pyridine-amidoxim-1-oxide (compound of formula III)

25.41 g (0.366 mol) of hydroxylamine hydrochloride and 36.6 g (0.305 mol) of 3-cyano-pyridine-1-oxide are dissolved in 540 ml of water, then 30.72 g (0.366 mol) of sodium-hydrogen carbonate is added in small portions. The reaction mixture is stirred for 2 hours at 20–25° C. The suspension is filtered, the precipitate is washed with water, dried, and recrystallized from a 9:1 mixture of methanol and water. The precipitate separating on cooling is filtered, washed and dried. 37.3 g (80%) of the title compound is obtained, which melts at 212–215° C. while decomposing.

IR: ν (KBr, cm$^{-1}$): 3407, 3337, 2840, 1660, 1470, 1429, 1397, 1227, 947, 925, 808, 792.

EXAMPLE 3 a) The preparation of N-[2-hydroxy-3-(1-piperidinyl)-propoxyl]-pyridine-1-oxide 3-carboxamidine (compound of formula I)

13.5 g (0.34 mol) of sodium-hydroxide is dissolved in 35 ml of water, and the solution is cooled to 10° C. 60.75 g (0.34 mol) of 2-hydroxy-4-azoniaspiro[3,5]nonane chloride is added, and the reaction mixture is stirred for 40 minutes at 5–10° C. 540 ml of ethanol and 40.5 g (0.26 mol) 3-pyridine-amidoxim-1-oxide are added. The reaction mixture is heated for 2 hours under a reflux condenser. The solution is cooled, the separated sodium chloride is filtered, washed with 100 ml of ethanol, and then the solvent is evaporated off. The evaporation residue is digerated with diethyl-ether, the precipitate separated in the cooler is filtered, washed with ether, dried, and crystallized hot from isopropanol. 47.4 g (62%) of the title compound is obtained, which melts at 130–132.5° C.

IR: ν (KBr, cm$^{-1}$): 3397, 3189, 2928, 1647, 1610, 1570, 1505, 1425, 1247, 1226, 1033, 942, 901, 782, 662, 531.

b) The preparation of N-[2-hydroxy-3-(1-piperidinyl)-propoxy]-pyridine-1-oxide-3-carboxamidine monohydrochloride The obtained base of formula (I) is dissolved in ethanol, and 1 equivalent of ethanolic hydrochloric acid solution is added. The solution is evaporated, and the residue is digerated with isopropanol. The separated salt is filtered, washed and dried. N-[2-hydroxy-3-(1-piperidinyl)-propoxy]-pyridine-1-oxide-3-carboxamidine monohydrochloride is obtained. Melting point: 142–144.5° C.

$^1$H-NMR: (Solvent: DMSO; referent: DMSO; MHz: 75.4) δ [ppm]: 9.65 (bs, 1H, NH$^+$); 8.42 (s, 1H, 2-pyridine); 8.22 (d, 1H, 6-pyridine); 7.58 (d, 1H, 4-pyridine); 7.42 (t, 1H, 5-pyridine); 6.50 (s, 2H, NH$_2$); 5.72 (d, 1H, OH); 4.24 (bm, 1H, OCH); 3.86 (m, 2H, NOCH$_2$); 3.42 (m, 2H, 2×NCH$_{eq}$); 3.18 (m, 2H, NCH$_2$); 2.92 (m, 2H, 2×NCH$_{ax}$); 1.36–1.8 (m, 6H, 3-, 4- and 5-piperidine).

$^{13}$C-NMR: (Solvent: DMSO; Referent: DMSO; MHz: 75.4) □ [ppm]: 148.2 (CNO); 139.2 (2-pyridine); 135.9 (6-pyridine); 131.8 (3-pyridine); 126.3 (5-pyridine); 122.9 (4-pyridine); 74.9 (CHOH); 63.6 (NOCH$_2$); 58.9 (NCH$_2$); 53.6 and 51.9 (2C, 2×piperidine NCH$_2$); 22.1 (2C, 3- and 5-piperidine); 21.2 (4-piperidine).

Cl$^-$ content According to Mohr (calculated/measured): 10.7/10.45.

EXAMPLE 4 a) The preparation of N-[2-hydroxy-3-(1-piperidinyl)-propoxy]-pyridine-1-oxide-3-carboximidoyl Chloride (Compound of formula V)

The solution of 6.1 g (0.088 mol) of sodium nitrite in 40 ml of water is added dropwise at −5–0° C. to the solution of 20 g (0.068 mol) of N-[2-hydroxy-3-(1-piperidinyl)-propoxy]-pyridine-1-oxide-3-carboxamidine in 110 ml of 1M hydrochloric acid cooled to −5° C. The reaction mixture is stirred for 1.5 hours at between −5° C. and 0° C., and then, by intense cooling (t<7° C.), the mixture is alkalified with a 7M NaOH solution to pH=10.5–11.5. The solution is extracted three times with 180 ml of dichloro-methane, the organic phases are pooled, dried on anydrous MgSO$_4$, filtered, washed and evaporated. The thus obtained thick oil is digerated in 130 ml of methyl tert-butyl ether. The suspension is refrigerated for 12 hours, the following day the precipitate is filtered, washed and dried. 18 g (85%) of the title compound is obtained, which melts at 90–91.5° C.

IR: υ (KBr, cm$^{-1}$): 3224, 2935, 2800, 2780, 1570, 1555, 1428, 1301, 1290, 1200, 1100, 1054, 1044, 1023, 1015, 995, 845, 827, 785, 710, 665.

b) The preparation of N-[2-hydroxy-3-(1-piperidinyl)-propoxy]-pyridine-1-oxide-3-carboximidoyl chloride maleate 50 g of the base prepared as described above is dissolved in 50 ml of acetone, and an equivalent amount (1.85 g) of maleic acid is added to it. The separated precipitate is filtered, washed with acetone and dried. The product is recrystallized from ethanol. 6.0 g (87%) of N-[2-hydroxy-3-(1-piperidinyl)-propoxy]-pyridine-1-oxide-3-carboximidoyl chloride maleate (1:1) is obtained, which melts at 150.5–154.5° C.

$^1$H-NMR: (Solvent: DMSO; Referent: DMSO; MHz: 300) □ [ppm]: 8.55 (s, 1H, 2-pyridine); 8.35 (d, 1H, 6-pyridine); 7.68 (d, 1H, 4-pyridine); 7.55 (m, 1H, 5-pyridine); 6.00 (s, 2H, CH═CH); 4.23–4.48 (m, 3H, CH—OH and NOCH$_2$); 2.95–3.50 (m, 6H, 3 NCH$_2$); 1.20–1.90 (m, 6H, piperidine: 3 CH$_2$).

$^{13}$C-NMR: (Solvent: DMSO; Referent: DMSO; MHz: 75.4) □ [ppm]: 167.6 (2C, 2COOH); 141.0 (2-pyridine), 136.8 (6-pyridine); 136.4 (2C, CH═CH); 133.4 (CCl); 131.9 (3-pyridine); 127.2 (4-pyridine); 123.6 (5-pyridine); 77.9 (NOCH$_2$); 63.6 (CH$_2$N); 58.3 (CHOH); 52.0–55.0 (2C, piperidine: 2NCH$_2$); 22.6 and 21.7 (3C, piperidine: 3CH$_2$).

c) The preparation of (R,S)-N-[2-hydroxy-3-(1-piperidinyl)-propoxy]-pyridine 1-oxide-3-carboximidoyl-chloride monohydrochloride 0.64 g (2.0 mmoles) of (R,S)-N-[2-hydroxy-3-(1-piperidinyl)-propoxy]-pyridine-1-oxide-3-carboximidoyl-chloride base is dissolved in 20 ml of ethylacetate and 0.64 ml of the etheric solution of 3.2 M hydrochloric acid is added while stirring. A sticky precipitate is formed. After evaporating the solvent, 15 ml of acetone is added and refrigerated overnight. The precipitate is crystallized with the addition of some drops of ethanol, then the white hygroscopic material is quickly filtered, and dried in a desiccator over phosphorous-pentoxide.

Yield: 0.4 g (56.3%).

Melting point: 115–122° C.

Cl % (ionic): 11.2% (theoretical: 10.1%).

IR (KBr, cm$^1$): 3240, 3060, 2950, 2860, 2760, 1575, 1550, 1465, 1450, 1431, 1310, 1293, 1240, 1195, 1155, 1120, 1090, 1075, 1045, 1005, 945, 925, 830, 792, 715, 671, 550.

EXAMPLE 5 a) The preparation of (R)-(+)-N-[2-hydroxy-3-(1-piperidinyl)-propoxy]-pyridine-1-oxide-3-carboximidoyl Chloride by the resolution of the raceme compound 54 g (0.172 mol) of raceme N-[2-hydroxy-3-(1-piperidinyl)-propoxy]-pyridine-1-oxide-3-carboximidoyl chloride is dissolved in 720 ml of dry ethanol. After complete dissolution, 64.7 g (0.172 mol) of (−)-dibenzoyl-L-tartaric acid monohydrate is added. After seeding, it is crystallized at room temperature, then the separated precipitate is filtered, washed and dried. The obtained residue is crystallized twice from dry ethanol. 38 g (65%) of (R)-(+)-N-[2-hydroxy-3-(1-piperidinyl)-propoxy]-pyridine-1-oxide-3-carboximidoyl chloride dibenzoyl-L-tartaric acid salt is obtained.

The thus obtained 38 g (0.056 mol) of tartaric acid salt is then added to 230 ml of 1M $K_2CO_3$ solution, and the mixture is extracted with 3×225 ml of dichloro-methane. The organic phases are pooled, dried on anhydrous MgSO4, treated with charcoal, filtered and evaporated. The compound is obtained in a pure form from the crude base by crystallization with hexane. Yield: 14.0 g (80%). Melting point: 91–93° C.

IR: υ (KBr, cm$^{-1}$): 3181, 2938, 2800, 1575, 1555, 1473, 1431, 1350, 1300, 1286, 1251, 1232, 1186, 1162, 1555, 1095, 1055, 1044, 1020, 1011, 963, 928, 908, 899, 850, 831, 803, 700, 670.

$^1$H-NMR: (Solvent: CDCl$_3$; Referent: CDCl$_3$; MHz: 300) δ [ppm]: 8.62 (s, 1H, 2-pyridin), 8.20 (d, 1H, 6-pyridine); 7.64 (m, 1H, 4-pyridine); 7.26 (m, 1H, 5-pyridine); 4.24 (d, 2H, NOCH$_2$); 4.02 (m, 1H, OCH); 2.58 (m, 2H, NCH$_2$); 2.32 (m, 4H, 2×piperidine NCH$_2$); 1.5–1.6 (m, 4H, 3- and 5-piperidine); 1.42 (m, 2H, 4-piperidine).

$^{13}$C-NMR: (Solvent: CDCl$_3$; Referent: CDCl$_3$; MHz: 75.4) δ[ppm]: 140.0 (2-pyridine); 137.5 (6-pyridine); 132.7 (CNO); 132.4 (3-pyridine); 125.5 (5-pyridine); 123.8 (4-pyridine); 78.8 (OCH); 64.9 (NOCH$_2$); 60.6 (NCH$_2$); 54.6 (2C, 2×piperidin NCH$_2$); 26.0 (2C, 3- and 5-piperidine); 24.1 (4-piperidine).

b) The preparation of (R)-(+)-N-[2-hydroxy-3-(1-piperidinyl)-propoxy]-pyridine-1-oxide-3-carboximidoyl chloride maleate 18.0 g of crude (evaporation residue from the process a/) or isolated base is dissolved in 62 ml of acetone, and then the solution of 6.6 g maleic acid in 46 ml of acetone is added. The precipitate separating on cooling is filtered, washed with 10 ml of acetone and dried. The precipitate (approx. 23 g) is crystallized from 120 ml of hot ethanol. The precipitate separating on cooling is filtered, washed and dried.

Yield: 20 g (82%).

Melting point: 132.0–133.5° C.

Enantiomer ratio: 98/2 (HPLC measurement on a Chiral AGP 100×4 mm column).

IR: υ (KBr, cm$^{-1}$): 3270 (b); 2935; 2850, 1581; 1484; 1436; 1349; 1293 (s); 1205 (s); 1067; 1047; 999 (s); 865 (s); 830; 800, 682, 558.

The $^1$H-NMR and $^{13}$C-NMR spectra were the same as those of the raceme compound (Example 4/b).

c) The preparation of (R)-(+)-N-[2-hydroxy-3(1-piperidinyl)-propoxy]-pyridine-1-oxide-3-carboximidoyl chloride citrate 2.43 g (7.75 mmol) of (+)-/R/-N-[2-hydroxy-3-(1-piperidinyl)-propoxy]-pyridine-1-oxide-3-carboximidoyl chloride is dissolved in 15 ml of acetone while heating gently, then 5 ml of the solution of 1.63 g (7.75 mmol) of citric acid in acetone is added. The separating white sticky substance becomes a powder on the addition of 5 ml of methanol. The solution is refrigerated until the following day. The precipitate is filtered, washed with acetone, and dried. 3.99 g (98%) of product is obtained.

Melting point: 163–165° C.

$^{13}$C-NMR: (Solvent: DMSO/CDCl$_3$; Referent: CDCl$_3$; MHz: 75.4) δ [ppm]: 175.2 (COOH); 169.9 (2C, 2COOH); 138.6 (2-pyridine), 134.7 (4-pyridine); 131.0 (CCl); 129.9 (3-pyridine); 125.0 (6-pyridine); 122.5 (5-pyridine); 76.0 (COH); 69.7 (CHOH); 62.0 (NOCH$_2$); 57.0 (CH$_2$N); 51.5 (2C, 2×piperidine NCH$_2$); 42.3 (2C, 2×CH$_2$); 21.0 (2C, 3- and 5-piperidine CH$_2$); 20.0(4-piperidine).

d) The preparation of (R)-(+)-N-[2-hydroxy-3-(1-piperidinyl)-propoxy]-pyridine-1-oxide-3-carboximidoyl-chloride monohydrochloride 0.88 g (2.8 mmoles) of (R)-(+)-N[2-hydroxy-(1-piperidinyl)-propoxy]-pyridine-1-oxide-3-carboximidoyl-chloride base (prepared from its maleate using dichloromethane/10% aqueous sodium-carbonate solution) is dissolved in 25 ml of ethylacetate and 0.87 ml of the etheric solution of 3.2 M hydrochloric acid is added while stirring.

After evaporating the solvent, 15 ml of acetone is added to the residual sticky oil and crystallized with with the addition of some drops of ethanol. The white compound is filtered and washed with acetone and diethyl ether.

Yield: 0.8 g (81.6%).

Melting point: 127–131° C.

Cl %(ionic): 12.1%(theoretical: 10.1%).

IR (KBr, cm$^{-1}$): 3510, 3365, 3120, 3075, 2950, 2930, 2890, 2855, 2725, 2655, 2568, 2527, 1620, 1600, 1562, 1483, 1460, 1428, 1407, 1350, 1335, 1294, 1238, 1197, 1170, 1125, 1072, 1019, 1002, 942, 910, 877, 859, 825, 802, 708, 671, 629, 608, 556, 501.

e) The preparation of (R)-(+)-N-[2-hydroxy-3-(1-piperidinyl)-propoxy]-pyridine-1-oxide-3-carboximidoyl-chloride dihydrochloride 0.65 g (2.0 mmoles) of (R)-(+)-N-[2-hydroxy-3-(1-piperidinyl)-propoxy]-pyridine-1-oxide-3-carboximidoyl-chloride base (prepared from its maleate using dichloromethane/10% aqueous sodium-carbonate solution) is dissolved in 25 ml of ethylacetate and 1.4 ml of the etheric solution of 3.2 M hydrochloric acid is added while stirring.

After evaporating the solvent, 15 ml of acetone is added to the residual sticky oil and crystallized with the addition of some drops of ethanol. The white compound is filtered and washed with cold acetone and diethylether.

Yield: 0.4 g (55.0%).

Melting point: 160–164° C.

Cl % (ionic): 18.5% (theoretical: 18.3%).

IR (KBr, cm$^{-1}$): 3510, 3365, 3120, 3075, 2950, 2930, 2890, 2855, 2725, 2568, 2527, 1620, 1600, 1562, 1483, 1460, 1428, 1407, 1350, 1335, 1294, 1238, 1197, 1170, 1125, 1072, 1019, 1002, 942, 910, 877, 859, 825, 802, 708, 671, 629, 608, 556, 501.

EXAMPLE 6 a) The preparation of (S)-(+)-N-[2-hydroxy-3-(1-piperidinyl)-propoxy]-pyridine-1-oxide-3-carboxamidine by the resolution of the raceme compound 1.74 g (5.9 mmol) of raceme N-[2-hydroxy-3-(1-piperidinyl)-propoxy]-pyridine-1-oxide-3-carboxamidine is dissolved in 15 ml of ethanol, and then 2.1 g (5.9 mmol) of /+/-dibenzoyl-D-tartaric acid is added to the solution. It is crystallized at room temperature, the separated salt is filtered, washed with ethanol, and dried. The 2.1 g product is then crystallized twice from ethanol to give 0.33 g (17%) of (S)-(+)-N-[2-hydroxy-3-(1-piperidinyl)-propoxy]- pyridine-1-oxide-3-carboxamidine dibenzoyl-D-tartaric acid salt (melting point: 156–158° C.).

The (S)-(+)-N-[2-hydroxy-3-(1-piperidinyl)-propoxy]-pyridine-1-oxide-3-carbox-amidine is liberated from the obtained salt by distribution between 2M $K_2CO_3$ solution and chloroform, evaporation of the chloroform solution, and isolation with ether. Yield: 0.11 g (13%).

Melting point: 123–126° C.

IR: υ (KBr, cm$^{-1}$): 3398, 3188, 2936, 2800, 1647, 1600, 1560, 1500, 1426, 1245, 1226, 1033, 942, 907, 800, 667.

Rotation: $[\alpha]_D$=+4,5° (c=1, methanol).

To determine the optical purity of the product, a small sample is transformed into the corresponding chloro compound, (S)-(−)-N-[2-hydroxy-3-(1-piperidinyl)-propoxy]-pyridine-1-oxide-3-carboximidoyl chloride by the diazotation process described in example 4/a, and its optical purity is determined by HPLC on a Chiral AGP column. Determined by this method, the optical purity of the product gained by the described resolution process is 96%.

b) The preparation of (R)-(−)-N-[2-hydroxy-3-(1-piperidinyl)-propoxy]-pyridine-1-oxide-3-carboxamidine by the resolution of the raceme compound Following the process described in a), but this time using (−)-dibenzoyl-L-tartaric acid for the resolution, the yield of the obtained dibenzoyl-tartarate salt is 20%, and its melting point is 156.5–158° C. After liberating the base from this, (R)-(−)-N-[2-hydroxy-3-(1-piperidinyl)-propoxy]-pyridine-1-oxide-3-carboxamidine is obtained of optical purity of 96%.

Rotation: $[\alpha]_D$=−4,5° (c=1, methanol).

Its melting point and IR spectrum are the same as those of the other enantiomer.

c) The preparation of (S)-(+)-N-[2-hydroxy-3-(1-piperidinyl)-propoxy]-pyridine-1-oxide-3-carboxamidine monohydrochloride The (S)-(+)-N-[2-hydroxy-3-(1-piperidinyl)-propoxy]-pyridine-1-oxide-3-carbox-amidine base prepared by the example 6/a is dissolved in isopropanol. Equivalent amount of isopropanolic hydrochloric acid solution is added. The crystallized monohydrochloride salt is filtered and dried.

Melting point: 164–165.5° C.

IR: υ (KBr, cm$^{-1}$): 3400, 3317, 3191, 2948, 2862, 2710, 2690, 2655, 1651, 1562, 1429, 1407, 1308, 1232, 1112, 1052, 1010, 962, 944, 880, 797, 670.

d) The preparation of (S)-(+)-N-[2-hydroxy-3-(1-piperidinyl)-propoxy]-pyridine-1-oxide-3-carboxamidine maleate The maleate salt of the (S)-(+)-N-[2-hydroxy-3-(1-piperidinyl)-propoxy]-pyridine-1-oxide-3-carboxamidine base prepared by example 6/a is prepared by the addition of equivalent maleic acid in an isopropanolic solution.

Melting point: 148–150.5° C.

IR: υ (KBr, cm$^{-1}$): 3465, 3381, 3360, 3092, 3058, 2945, 2855, 1651, 1619, 1582, 1561, 1499, 1474, 1459, 1451, 1432, 1318, 1352, 1250, 1230, 1204, 1086, 1035, 1015, 931, 867, 805, 797, 782, 696, 675, 564.

EXAMPLE 7

The preparation of (S)-(−)-N-[2-hydroxy-3-(1-piperidinyl)-propoxy]-pyridine-1-oxide-3-carboximidoyl chloride by diazotation By diazotation according to the process described in example 4. followed by the decomposition of the diazonium salt, 5 g of the (S)-(+)-N-[2-hydroxy-3-(1-piperidinyl)-propoxy]-pyridine-1-oxide-3-carboxamidine, prepared under example 6/a by the resolution of N-[2-hydroxy-3-(1-piperidinyl)-propoxy]-pyridine-1-oxide-3-carboxamidine, is transformed into (S)-(−)-N-[2-hydroxy-3-(1-piperidinyl)-propoxy]-pyridine-1-oxide-3-carboximidoyl chloride. 4.4 g (82%) of the product is obtained. The characteristics of the obtained product are the same as those given for the other enantiomer in example 5.

The base is reacted with maleic acid by the process given in example 5, and thus the corresponding maleate salt is obtained, whose characteristics are also the same as those given in example 5.

What is claimed is:

1. N-[2-hydroxy-3-(1-piperidinyl)-propoxy]-pyridine-1-oxide-3-carboxamidine and its acid addition salts.

2. (R)-(−)-N-[2-hydroxy-3-(1-piperidinyl)-propoxy]-pyridine-1-oxide-3-carboxamidine and its acid addition salts.

3. (S)-(+)-N-[2-hydroxy-3-(1-piperidinyl)-propoxy]-pyridine-1-oxide-3-carboxamidine and its acid addition salts.

4. Process for the preparation of N-[2-hydroxy-3-(1-piperidinyl)-propoxy]-pyridine-1-oxide-3-carboximidoyl chloride and its acid addition salts, comprising:
   a) the diazotation of N-[2-hydroxy-3-(1-piperidinyl)-propoxy]-pyridine-1-oxide-3-carboxamidine by reacting with an alkali-nitrite in the presence of hydrochloric acid, or
   b) the diazotation of N-[2-hydroxy-3-(1-piperidinyl)-propoxy]-pyridine-1-oxide-3-carboxamidine by reacting with an alkali-nitrite in the presence of hydrochloric acid, and the transformation of the obtained base into an acid addition salt.

5. Process for the preparation of (R)-(+)-N-[2-hydroxy-3-(1-piperidinyl)-propoxy]-pyridine-1-oxide-3-carboximidoyl chloride and (S)-(−)-N-[2-hydroxy-3-(1-piperidinyl)-propoxy]-pyridine-1-oxide-3-carboximidoyl chloride, and their acid addition salts, comprising
   a) the diazotation of (R)-(−)-N-[2-hydroxy-3-(1-piperidinyl)-propoxy]-pyridine-1-oxide-3-carboxamidine or (S)-(+)-N-[2-hydroxy-3-(1-piperidinyl)-propoxy]-pyridine-1-oxide-3-carboxamidine by reacting with an alkali-nitrite in the presence of hydrochloric acid, or
   b) the resolution of N-[2-hydroxy-3-(1-piperidinyl)-propoxy]-pyridine-1-oxide-3-carboxamidine, and the diazotation of the obtained optically active (R)-(−) enantiomer or (S)-(+) enantiomer in the presence of hydrochloric acid by reacting with an alkali-nitrite, or
   c) the diazotation of N-[2-hydroxy-3-(1-piperidinyl)-propoxy]-pyridine-1-oxide-3-carboxamidine in the presence of hydrochloric acid by reacting with an alkali-nitrite, and the isolation of the required (R)-(+) or (S)-(−) enantiomer by resolving the obtained raceme N-[2-hydroxy-3-(1-piperidinyl)-propoxy]-pyridine-1-oxide-3-carboximidoyl chloride, or
   d) the transformation of (R)-(+)-N-[2-hydroxy-3-(1-piperidinyl)-propoxy]-pyridine-1-oxide-3-carboximidoyl chloride or (S)-(−)-N-[2-hydroxy-3-(1-piperidinyl)-propoxy]-pyridine-1-oxide-3-carboximidoyl chloride, prepared by any of the process variants under a)–c), into an acid addition salt.

* * * * *

UNITED STATES PATENT AND TRADEMARK OFFICE
CERTIFICATE OF CORRECTION

PATENT NO. : 7,126,002 B2
APPLICATION NO. : 10/257755
DATED : October 24, 2006
INVENTOR(S) : Ürögdi et al.

It is certified that error appears in the above-identified patent and that said Letters Patent is hereby corrected as shown below:

Column 2, line 17, change "propoxyl" to -- propoxy] --

Column 2, line 64, change "N-(2" to -- N-[2 --

Column 2, line 67, "piperidine" to -- piperidinyl --

Column 3, line 28, change "preparing" to -- preparation --

Column 3, line 40, change "N-(2" to -- N-[2 --

Column 3, line 41, change "propoxyl" to -- propoxy] --

Column 5, line 15, change "propoxyl]" to -- propoxy] --

Column 6, line 55, change "cm$^1$" to -- cm$^{-1}$ --

Column 8, line 10, change "hydroxy-(1-" to -- hydroxy-3-(1- --

Column 8, line 18, delete second occurrence of "with"

Signed and Sealed this

Fifth Day of June, 2007

JON W. DUDAS
*Director of the United States Patent and Trademark Office*